US007439856B2

(12) United States Patent
Weiner et al.

(10) Patent No.: US 7,439,856 B2
(45) Date of Patent: Oct. 21, 2008

(54) HEALTH CARE PATIENT STATUS EVENT PROCESSING AND REPORTING

(75) Inventors: Herbert S. Weiner, Portland, OR (US); Douglas S. Adams, Tigard, OR (US); Jon K. F. Fo, Beaverton, OR (US); Koo Lee, Hillsboro, OR (US); Steven D. Baker, Beaverton, OR (US); Eric G. Petersen, Aloha, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 306 days.

(21) Appl. No.: 11/494,245

(22) Filed: Jul. 27, 2006

(65) Prior Publication Data
US 2007/0013511 A1    Jan. 18, 2007

Related U.S. Application Data

(63) Continuation-in-part of application No. 11/031,736, filed on Jan. 7, 2005, now Pat. No. 7,382,247, which is a continuation of application No. 10/806,770, filed on Mar. 22, 2004, now abandoned.

(60) Provisional application No. 60/554,706, filed on Mar. 20, 2004.

(51) Int. Cl.
*G08B 1/08*       (2006.01)
*G08B 23/00*   (2006.01)
*A61B 5/00*     (2006.01)

(52) U.S. Cl. .................. 340/539.12; 340/539.13; 340/539.18; 340/573.1; 600/300; 600/301; 128/903; 128/904; 702/19

(58) Field of Classification Search ............ 340/539.12, 340/539.13, 539.18; 600/301; 128/904
See application file for complete search history.

(56) References Cited

U.S. PATENT DOCUMENTS

| 5,942,986 A * | 8/1999 | Shabot et al. .............. 340/7.29 |
| 6,292,687 B1 * | 9/2001 | Lowell et al. ............... 600/515 |
| 6,842,774 B1 * | 1/2005 | Piccioni ...................... 709/207 |
| 6,998,978 B2 * | 2/2006 | Kirkeby ................. 340/539.12 |
| 7,301,451 B2 * | 11/2007 | Hastings ................ 340/539.12 |

\* cited by examiner

*Primary Examiner*—Donnie L Crosland
(74) *Attorney, Agent, or Firm*—Hiscock & Barclay, LLP; Peter J. Bilinski

(57) ABSTRACT

The invention provides a method and system for communicating, processing and responding to information reporting the status of health care patients. In one aspect, the invention provides a procedure for allocating the attention of health care personnel to issues and events that are reported in association with health care patients located within a health care facility. In some embodiments, assignment of health care personnel to health care patients can be configured according to a set of directives. The directives can direct assignment of personnel based upon many criteria including, but not limited to, the identity and/or location of a health care patient, an issue or event associated with the status of the health care patient, the relative availability of other health care personnel to respond to the issue or event, or a combination thereof.

28 Claims, 7 Drawing Sheets

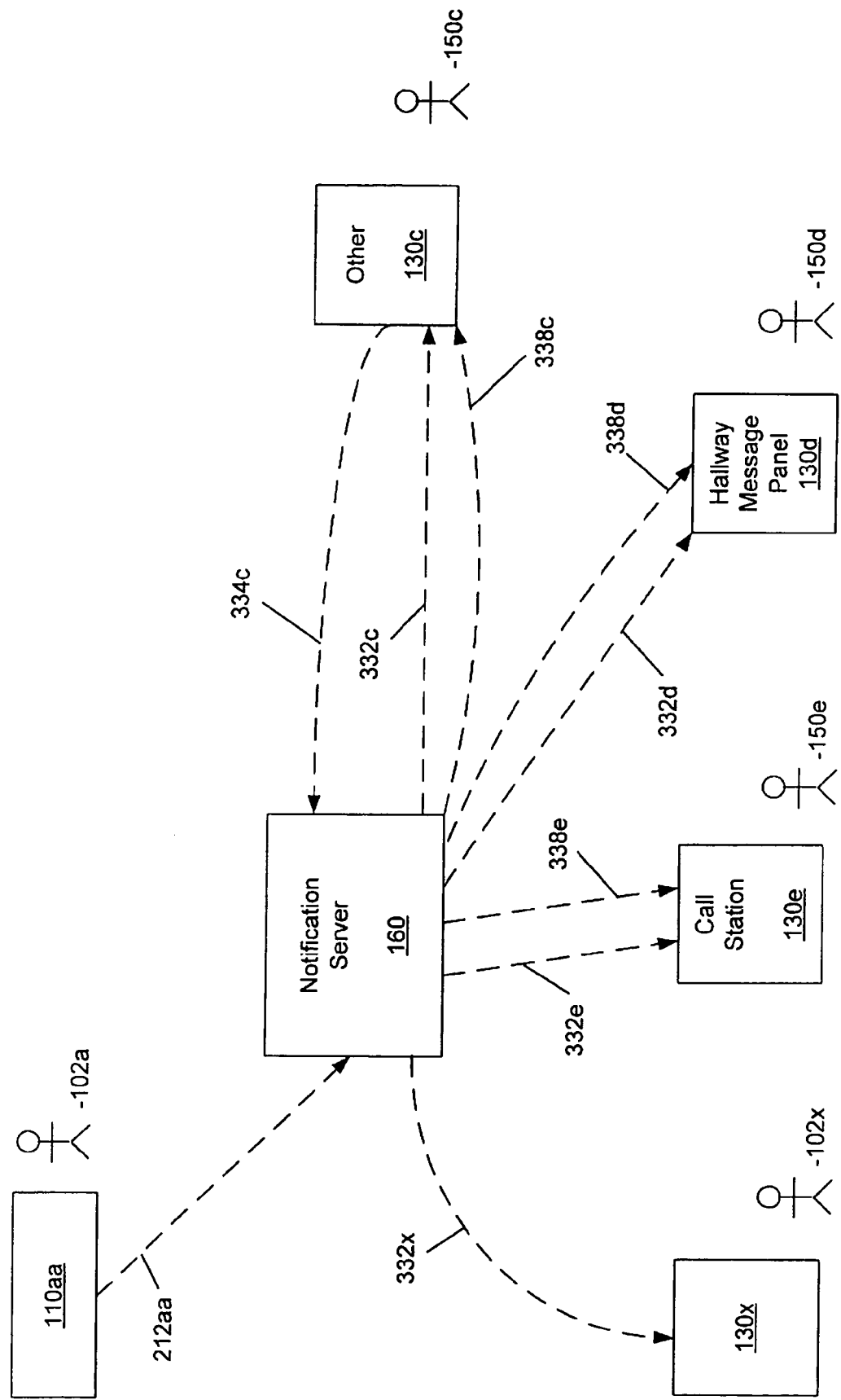

HEALTH CARE PATIENT STATUS EVENT PROCESSING AND REPORTING

CROSS-REFERENCE TO APPLICATION INCLUDING RELATED SUBJECT MATTER

This application is a continuation-in-part application under 37 C.F.R. 1.53(b) claiming benefit under 35 U.S.C. 120 to co-pending and commonly owned U.S. non-provisional patent application No. 11/031,736, entitled "Personal Status Physiologic Monitor System And Architecture And Related Monitoring Methods" and filed on Jan. 7, 2005, now U.S. Pat. No. 7,382,247 which is a continuation under 35 U.S.C. 120 of non-provisional application No. 10/806,770, also entitled "Personal Status Physiologic Monitor System And Architecture And Related Monitoring Methods" and filed Mar. 22, 2004 now abandoned which claims priority under 35 USC 119 (e)(1) to U.S. provisional patent application No. 60/554,706, entitled "Personal Status Physiologic Monitor System and Architecture And Related Monitoring Methods" and filed on Mar. 20, 2004.

This application also includes subject matter related to commonly owned and issued U.S. Pat. No. 6,616,606 titled "Patient Monitoring System". This application also includes subject matter related to commonly owned U.S. patent application Ser. No. 11/263,050, entitled "Attachment/Location Monitoring of a Signal Generating Entity" and filed on Oct. 31, 2005. All of the aforementioned patent(s) and patent application(s) are herein incorporated by reference in their entirety.

FIELD OF THE INVENTION

This invention relates generally to communicating and responding to information associated with the status of a health care patient, and in particular providing a system for enabling communication and response to health care patient status information over an extended distance to care takers associated with a health care facility.

BACKGROUND OF THE INVENTION

Various health care status reporting devices, such as those reporting a physiological status and/or a location status of a health care patient, are configured to communicate status information to within an auditory or visual range of the patient, or to locations extending farther distances from the health care patient. Health care personnel receive and respond to the status information.

SUMMARY OF THE INVENTION

The invention provides a method and system for communicating, processing and responding to information reporting the status of health care patients. In one aspect, the invention provides a procedure for allocating the attention of health care personnel to issues and events that are reported in association with health care patients located within a health care facility. In some embodiments, assignment of health care personnel to health care patients can be configured according to a set of directives. The directives can direct assignment of personnel based upon many criteria including, but not limited to, the identity and/or location of a health care patient, an issue or event associated with the status of the health care patient, the relative availability of other health care personnel to respond to the issue or event, or a combination thereof.

The foregoing as well as other objects, aspects, features, and advantages of the invention will become more apparent from the following description and from the claims.

BRIEF DESCRIPTION OF THE DRAWINGS

The objects and features of the invention can be better understood with reference to the claims and drawings described below. The drawings are not necessarily to scale, the emphasis is instead generally being placed upon illustrating the principles of the invention. Within the drawings, like reference numbers are used to indicate like parts throughout the various views. Differences between like parts may cause those like parts to be each indicated by different reference numbers. Unlike parts are indicated by different reference numbers.

FIG. 3C illustrates an exchange of messages constituting escalating actions in pursuit of assigning acceptance of responsibility to respond to the first communication.

DETAILED DESCRIPTION OF THE INVENTION

The following disclosure expands upon at least a portion of the subject matter disclosed within co-pending and commonly owned U.S. non-provisional patent application No. 11/031,736, filed Jan. 7, 2005) and titled "Personal Status Physiologic Monitor System and Architecture and Related Methods", also referred to herein as the parent patent application. Some reference numbers assigned to components within this disclosure that are like components also described within the parent patent application, may differ from those reference numbers of the parent application.

Figure 1A:
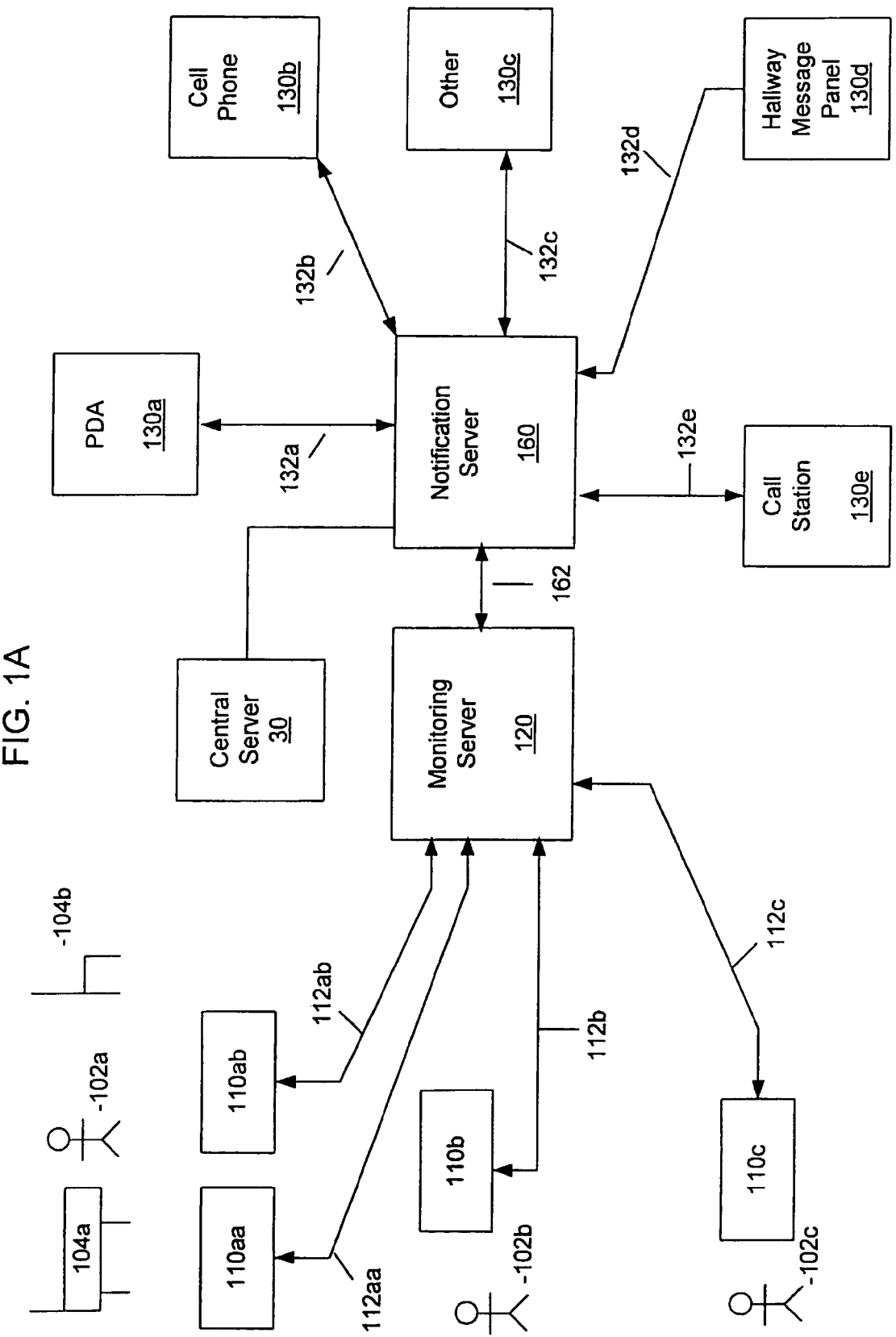
FIG. 1A illustrates an embodiment of a network that is configured for communicating information related to the status of health care patients.

FIG. 1A illustrates an embodiment of a network that is configured for communicating information related to the status of health care patients. As shown, the network includes a plurality of status reporting devices 110aa-110c, a monitoring server 120 and a notification server 160 and a plurality of respondent devices 130a-130e. As shown, the status reporting devices 110aa-110ab, are classified as non-patient worn patient monitoring devices 110aa-110ab, and may be associated with a particular patient at a particular time and location within the health care facility. The status reporting device 110aa has a wire line communications channel connection 112aa to a monitoring server 120. The status reporting device 110ab has a wireless communications channel connection to the monitoring server 120.

A non-patient worn monitoring device 110aa-110ab is typically attached to equipment assigned to a health care patient, such as a bed 104a or a chair 104b upon which a health care patient 102a reclines. This type of monitor is referred to as a bedside monitor 110aa-110ab and typically, the bed 104a or chair 104b is portable. A non-patient worn patient monitor 110a-110b is somewhat portable in that it can be relocated while it is attached to the bed 104a or the chair 104b that is portable and that can be relocated within a health care facility. Also, the non-patient worn monitor 110aa-110ab can be relocated from one bed 102a or chair 102b to another bed 102a or chair 102b and/or from one patient 102a-102c to another patient 102a-102c within a health care facility.

In some embodiments, the status reporting device 110ab is a bedside Propaq CS wireless patient monitor that is manufactured by Welch Allyn, Inc. This device provides a variety of patient vital signs monitoring functionality. This functionality includes wirelessly transmitting ECG signals, and information associated with other physiological parameters that are measured and received from a patient 100. Note that the Propaq CS is provided with a wireless option that supports either a wireline (hard wired) connection 110aa or a wireless connection 110ab. The Propaq CS without the wireless option supports only a wireline (hard wired) type of connection 110aa.

Preferably, this type of status reporting device 110aa-110ab has a bi-directional communications channel 112aa-112ab connection to the monitoring server 120. A bi-directional communications channel enables either end of the channel, namely the monitoring server 120 or the device 110aa-110ab, to receive a signal from the opposite end of the channel 112aa-112ab in order to verify that the opposite end is active (alive).

The status reporting device 110b, referred to as patient worn patient monitoring device 110b, is worn by and attached to a particular patient 102b located within the health care facility. The patient worn patient monitoring device 110b is portable in that it relocates with the movements of the patient, whether the patient is reclining in a bed or walking throughout the facility. Preferably, the status reporting device 110b has a bi-directional wireless communications channel connection to the monitoring server 120 for the same reasons as described above.

Patient monitoring devices, whether patient worn 110b or not patient worn 110aa-110ab, typically require some type of physical attachment to a patient 102a-102b in order to monitor at least one or more physiological attributes of the patient 102a-102b. In some embodiments, the patient worn monitoring device is a Micropaq wireless patient-worn monitoring device supplied by Welch Allyn Inc. The Micropaq patient-worn device is a patient-wearable device that provides a variety of patient vital signs monitoring functionality.

Patient vital signs monitoring devices, such as the Micropac, include functionality that wirelessly transmits ECG signals that are received from a patient as well as monitoring and transmitting other patient physiologic attributes, such as heart rate, body temperature and pulse oximetry. Typically, the communications are transmitted periodically over time to indicate to the receiver of the communication, namely the monitoring server 120, that the devices are attached to and monitoring a patient. Preferably, the vital signs monitoring device includes functionality that uses bidirectional communication to detect the loss of communication between itself and the monitoring server 120, and can generate a local audible alert indicating such a loss of communication.

The status reporting device 110c, referred to as a call button 110c, is typically located at a fixed location and proximate to a patient within the health care facility. The call button, when pressed (activated), transmits a communication via communication channel 112c indicating a request for attention from the patient 102c to health care providing personnel of the health care facility. In some embodiments, the status reporting device 110c has a one directional wireless communications channel connection to the monitoring server 120. In other embodiments, the status reporting device 110c has a bi-directional communication channel for the reasons described above.

In some circumstances, the communication 112c may not be urgent and could be made to request a glass of water, for example. In other circumstances, the communication 112d may be urgent and related to health problems, such as physical pain that the patient is experiencing at the time of the pressing of the call button 110d. Another example is where a patient falls and is unable to get up without assistance. Typically, the call button transmits, but does not receive, communications 112d.

The status reporting devices 110a-110c may also include a call button. The Propaq CS and the Micropaq wireless patient monitors each provide a call button that can be pressed (activated) by a patient or other personnel to call attention to the patient.

The monitoring server 120 is configured to relay the first communications 112aa-112c to a notification server 160 via a communications channel 162. The notification server 160 is configured to conditionally transmit a second communication via communications channels 132a-132e to one or more respondent devices 130a-130e, in response to receiving a first communication from a reporting device 110aa-110c, in accordance with a pre-determined set of rules, also referred to as directives.

Optionally the notification server 160 communicates with a server 30, also referred to as a central server 30. In some embodiments, the central server 30 functions to provide a repository of data, including patient, reporting device and respondent device related data. In this type of embodiment, the notification server 160 accesses the data via the central server 30. In some embodiments, the functionality of the central server 30 and the notification server 160 may be combined into a single server (not shown).

Figure 1B:
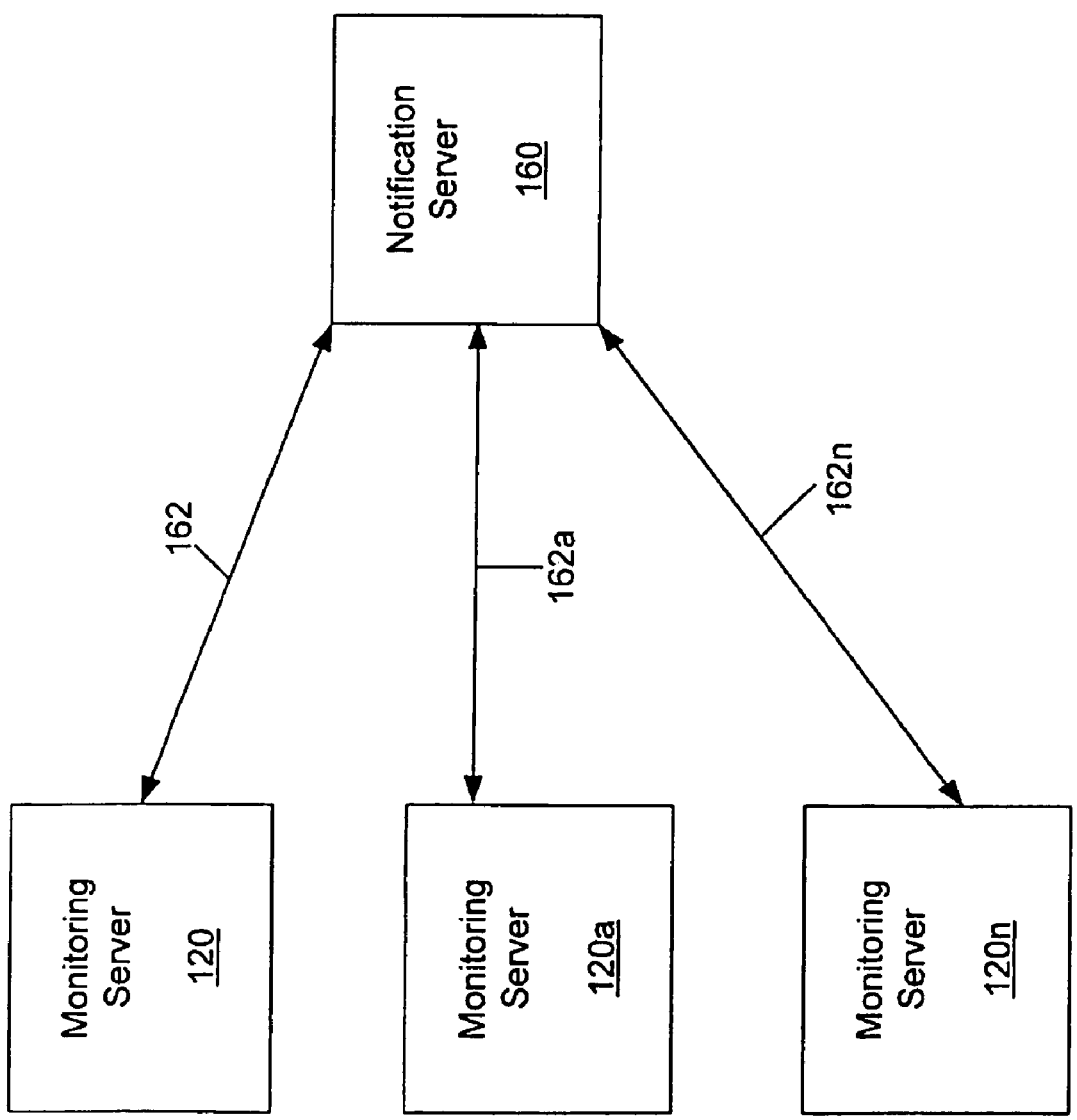
FIG. 1B illustrates a notification server that is configured to receive communications transmitted from various reporting devices via a plurality of monitoring stations.

FIG. 1B illustrates a notification server 160 that is configured to receive communications transmitted from various reporting devices via a plurality of monitoring stations 120-120n. As shown, communications received by the monitoring station 120 are relayed over communications channel 162, communications received by the monitoring station 120a are relayed over communications channel 162a and communications received by the monitoring station 120n are relayed over communications channel 162n.

Figure 1C:
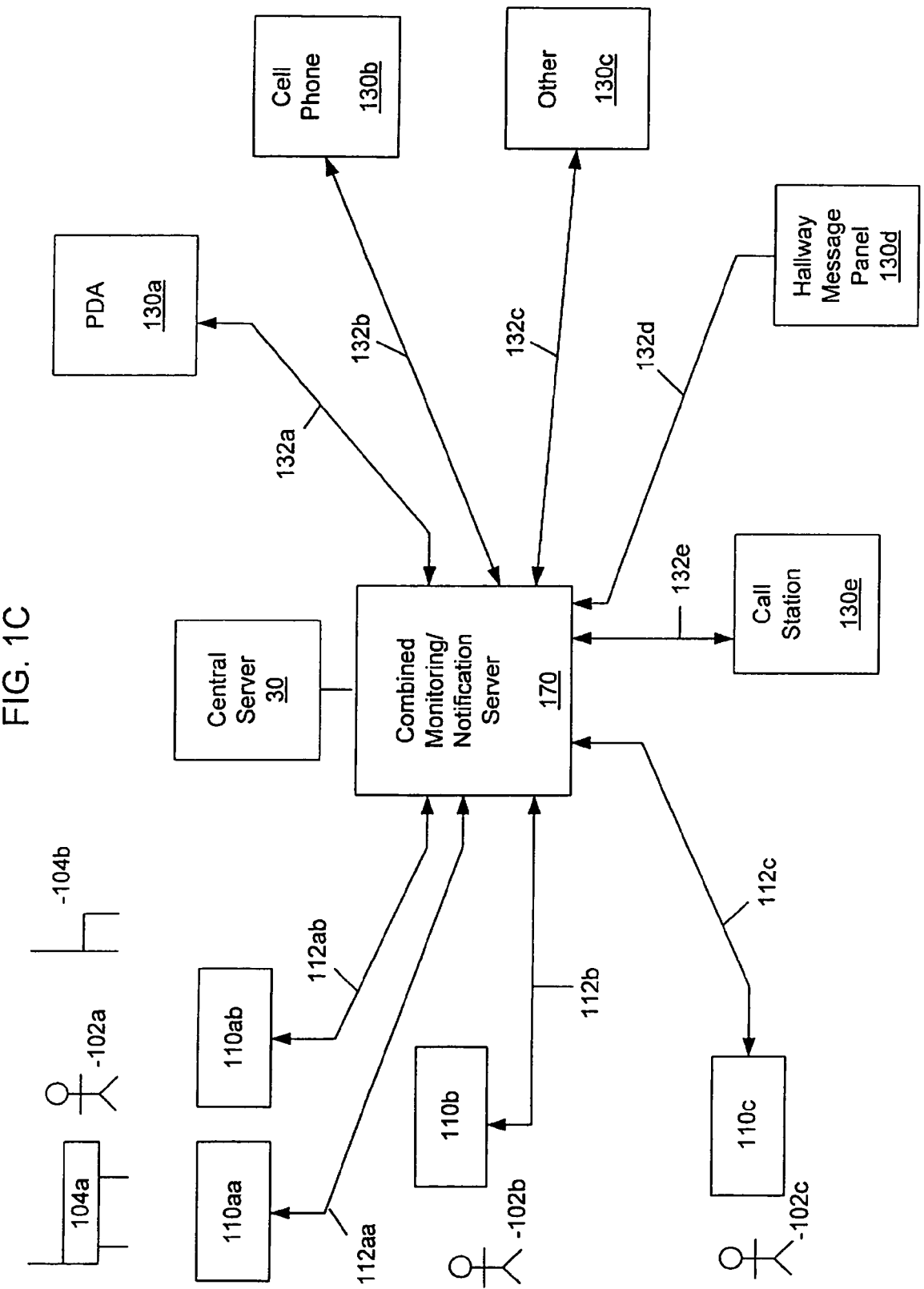
FIG. 1C illustrates a combined monitoring/notification server that is configured to combine the functionality of both the monitoring server and the notification server.

FIG. 1C illustrates a combined monitoring/notification server 170 that is configured to combine the functionality of both the monitoring server 120 and the notification server 160. As shown, the combined monitoring/notification server 170 directly receives communications transmitted from various reporting devices like the reporting devices 110aa-110c. The combined monitoring/notification server 170 directly transmits second communications to the respondent devices 130a-130e. The communications channels 162-162n of FIG. 1B are not required for this embodiment.

Figure 2:
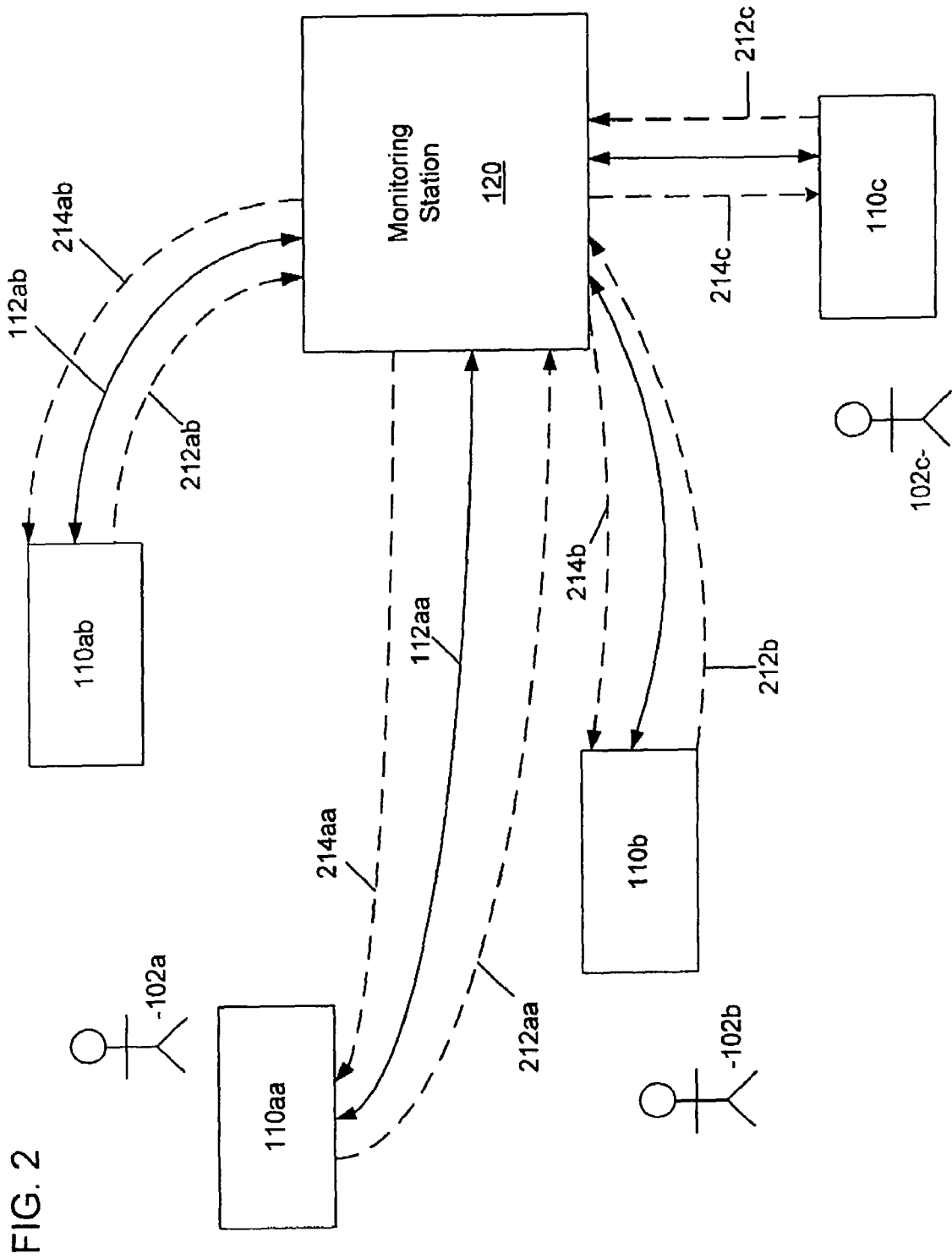
FIG. 2 illustrates an exchange of communications transmitted between the reporting devices and the monitoring server of FIG. 1A.

FIG. 2 illustrates an exchange of communications 212aa-212c, 214aa-214c transmitted between the reporting devices 110aa-110c and the monitoring server 120 via the communications channels 112aa-112c of FIG. 1. The first communications 212aa-212c, also referred to as reporting signals 212aa-212c, are transmitted, directly or indirectly, from the status reporting devices 110aa-110c to the monitoring server 120, also referred to as a central monitoring server 120. In one embodiment, the central monitoring server 120 is an Acuity central monitoring server manufactured by Welch Allyn, Inc.

The central monitoring server 120 receives the communications 212aa-212c and stores a representation of the information content of each communication 212aa-212c into its memory. The reporting signals are communicated via a predetermined communications interface exercised between each reporting device 110aa-110c and the central monitoring server 120. The communications interface is structured as a stack of one or more communications protocols. Each communications protocol is structured as a set of packets that each include one or fields of data. Each field of data includes information encoding a characteristic of each communication.

In some embodiments, the central monitoring server 120 transmits the communications 214aa-214c to the reporting devices 110aa-110c so that each reporting device 214aa-214c can verify that it has a live connection with the monitoring server 120. In some embodiments, if a reporting device 110aa-110c does not receive a communication from the monitoring server 120 within a pre-determined period of time, then the reporting device generates an audio or visual alarm to notify people within audible and visual range of the reporting device 110aa-110c of an apparent lack of a communications connection with the monitoring server 120.

In some embodiments, the monitoring server 120 and the notification server 125 are separated from each other as shown in FIGS. 1A-1B. In some embodiments, the monitoring server 120 and the notification server 160 are combined into one network node, referred to as the combined monitoring/notification server 170, as shown in FIG. 1C. For example, the Acuity Central Server manufactured by Welch Allyn is configured to perform the monitoring functions of the monitoring server 120, and the Welch Allyn Connectivity Server (WACS) manufactured by Welch Allyn is configured to perform the notification function of the notification server 160.

In some embodiments, each communication 212aa-212c transmitted from the reporting devices 110a-110c includes a reporting device address field that uniquely identifies the reporting device 110aa-110c and one or more event identifier fields. The monitoring server 120 is configured to access a mapping between the reporting device address, a unique patient identifier associated with the reporting device, one or more unique respondent identifiers associated with the unique patient identifier and at least one a respondent device associated with each unique respondent identifier. In some embodiments, the mapping is stored within a repository located on the central server 30.

In some embodiments, the reporting device 110aa-110c performs recognition of one or more events of interest and communicates 212aa-212c one or more event identifier fields, each representing the one or more events of interest, along with the reporting device address field to the monitoring server 120. Optionally, the reporting device 110aa-110c also communicates information that can be processed by other nodes in the network for recognition of various events of interest.

In some embodiments, for example, the reporting devices 110aa-110c include the Propaq and Micropaq devices that monitor cardio (heart) activity and are configured for cardio related event detection. These reporting devices 110aa-110c can measure heart beat rate over time and identify the occurrence of ventricle fibrillation or heart rates above a maximum rate or below a minimum rate. When ventricle fibrillation is detected for at least a minimum period of time, the communication 212aa-212c includes an event identifier field that indicates the occurrence of such an event.

In some embodiments, the monitoring server 120 performs recognition of one or more events via further processing of information communicated from the reporting device 110aa-110c. For example, in some embodiments, ECG waveform data is included within a first communication 212aa-212c that is transmitted from a reporting device 112aa-112c whether or not the reporting device itself 110aa-110c is configured to perform cardio related event detection, using the ECG wave form data as input. Optionally, the monitoring server 120 is configured to process the ECG waveform data to perform cardio related event detection and reporting.

Figure 3A:
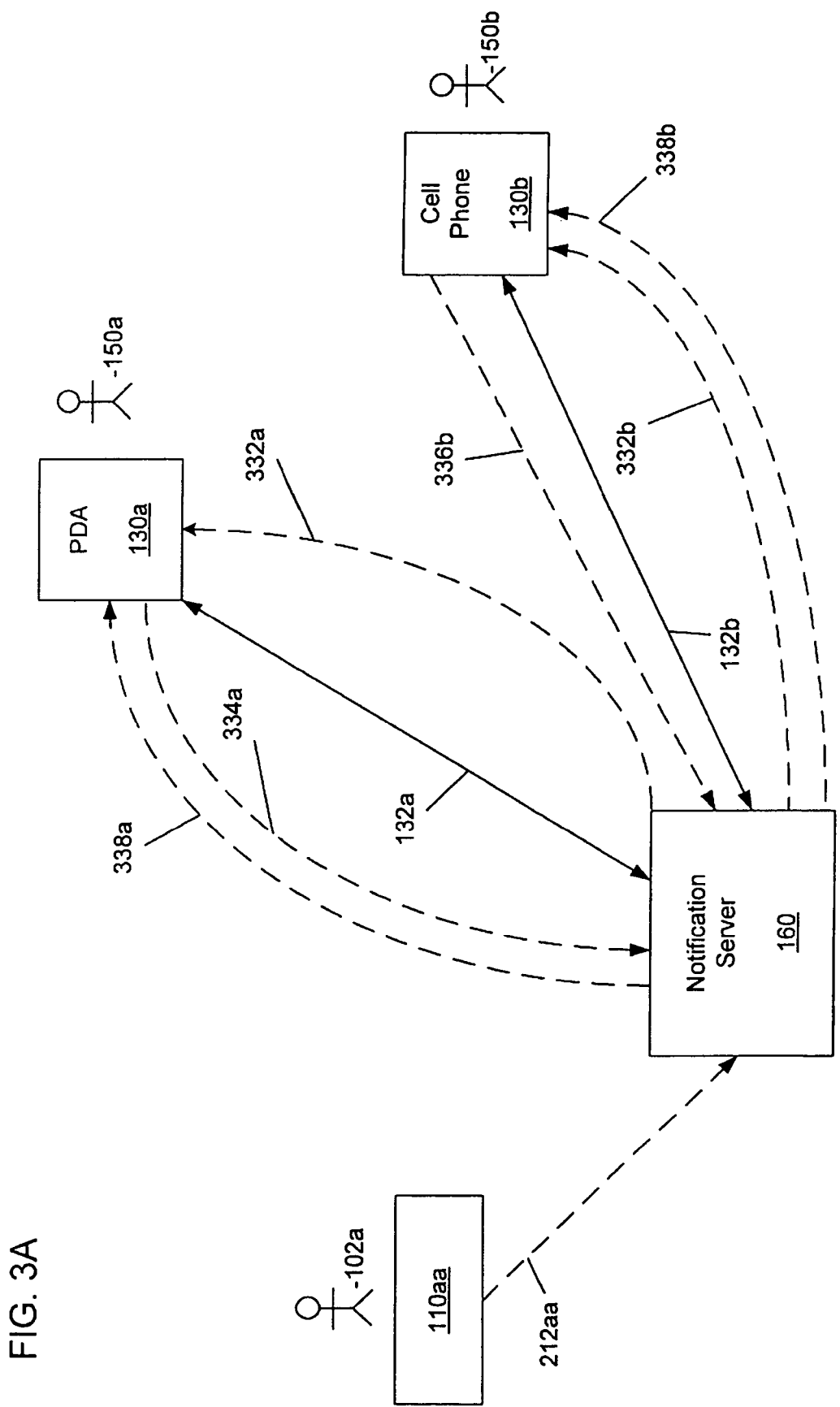
FIG. 3A illustrates a respondent notification scenario that results in an acceptance of responsibility to respond to a first communication.

FIG. 3A illustrates a respondent notification scenario that results in an acceptance of responsibility to respond to the first communication 212aa. The notification server 160 is configured to conditionally transmit a second communication 332a-332e to zero, one or more respondent devices 130a-130e, in response to receiving a first communication 212aa from a reporting device 110aa, in accordance with the pre-determined set of rules, referred to as the directives.

As shown this example respondent notification scenario, a first communication 212aa is indirectly received and processed by the notification server 160. The notification server 160 processes the communication 212aa and stores a representation of the information content of the communication 212aa into its memory. The following description applies to the example communication 212aa and can be applied to any other communication 212ab-212c received from a reporting device 110aa-110c.

In one embodiment of the invention, the following actions are performed in this scenario, preferably by software, residing within the notification server 160.

First, the notification server 160 searches through the information content of the communication 212aa and identifies a reporting device address associated with the reporting device 110aa and any events included therein. An event could constitute an alarm associated with a physiological measurement of a patient or could constitute an alarm associated with the physical location of a patient. Optionally, events are filtered to identify events of sufficient priority. If there are no events of sufficient priority, an attempt to notify a respondent is not made.

Else, automatic processing of the first communication 212aa proceeds as follows. If there are one or more events of sufficient priority, the notification server 160 proceeds to perform an automatic respondent notification procedure in order to notify a respondent.

In some embodiments, the automatic respondent notification procedure includes the following steps. First, the reporting device address is mapped to an identity of the reporting device 110aa and to a patient identifier using repository data. The patient identifier is mapped to one or more respondent identifiers that are members of a set of first escalation level group of respondents associated with the patient identifier. The respondent identifiers are mapped to respondents and to respondent devices.

In other embodiments, instead of mapping the patient identifier to one or more respondent identifiers, the automatic respondent notification procedure performs the mapping based upon information not limited to the patient identifier. For example, the mapping could be based upon a type of health problem that the patient is experiencing in association with the event of interest.

The repository stores associations between a reporting device identifier and a patient identifier and between a patient identifier and a patient, and between a patient and one or more groups of respondents. Each escalation level group of respondents is associated with an escalation level for responding to the first communication 212*aa* based upon the unique identity of the patient 102*a*. The repository also stores associations between respondent device identifiers and respondent devices 130*a*-130*e* and between a respondent devices 130*a*-130 *e* and respondents 150*a*-150*e*. The repository also stores a current availability status for each respondent device and for each respondent 150*a*-150*e*.

Next, a current availability status for each of the respondent devices 130*a*-130 *e* associated with a first escalation level group respondents, is tested via a respondent device test communication procedure. In some embodiments, the notification server 160 is configured to transmit a respondent device test communication, referred to as a "ping", to a respondent device 130*a*-130*e* in order to test whether the respondent device 130*a*-130*e* is available to receive a second communication 132*a*. A respondent device 130*a*-130*e* may be unavailable because it is located out of range, is powered off or has a discharged battery.

In some embodiments, a respondent device test communication procedure is executed to test the current availability of one or more respondent devices 130*a*-130*e* to receive a communication. Execution of this procedure can be according to criteria that is independent of the occurrence of a particular event.

For example, this procedure could be performed according to a schedule, to fixed time intervals (periodically) or on demand. If one or more respondent devices 130*a*-130 *e* are not available, one or more personnel of the health care facility can be notified to mitigate or correct this type of problem as early as possible, and ideally before the occurrence of a next event of interest associated with the one or more respondent devices 130*a*-130*e* that are determined to be currently unavailable.

If one or more respondent devices 130*a*-130*e*, of the first (lowest) escalation level group associated with the patient is available, then the notification server 160 transmits a second communication 132*a* to each of the available respondent devices 130*a*-130*e*.

In this example scenario, the first escalation level group associated with patient 110*aa* includes the (3) respondents 150*a*-150*c* and their respondent devices 130*a*-130 *c*, but only (2) respondent devices 130*a* and 130*b* are currently available. Respondent device 130*c* is not currently available.

A second communication 332*a*-332*b* is transmitted to the (2) respondent devices 130*a*-130*b*. The second communication 132*a* includes at least an identification of the patient 102*a* and of one or more events of interest associated with the patient 102*a*. Both the patient 102*a* and the events of interest associated with the patient 102a, are communicated to the reporting devices 130*a*-130*b*. The events of interest may have been previously recognized and indicated by the reporting device 110*aa* and/or recognized and indicated by the notification server 160, before being communicated to the respondent devices 130*a* and 130*b*.

Upon receiving the second communication 332*a*, the respondent device 130*a*, generates an indication, such as an audio and/or visual and/or vibratory indication, to its respondent (user) 150*a*. Likewise, the respondent device 130*b*, generates an indication, preferably an audio and/or visual and/or vibratory indication, to its respondent (user) 150*b*. The respondent device 130*a* is configured to provide a user interface that communicates at least some of the information content of the second communication 332*a*, to the respondent 150*a*. Likewise, the respondent device 130*b* is configured to provide a user interface that communicates at least some of the information content of the second communication 332*b*, to the respondent 150*b*.

Preferably, the respondent devices 130*a*-130*e* are configured to enable the respondent 150*a*-150*b* to transmit various types of response communications back to the notification server 160. The PDA 130*a* and cellular telephone 130*b* respondent devices, are each configured to enable a respondent (user) 150*a*-150*b* to transmit a response communication 334*a*, 336*b* back to the notification server 160. The respondent device 130*c* is a generic communications device 130*c* having the same response capabilities as the respondents devices 130*a*-130*b*.

Generally, in response to receiving a communication 332*a*, a respondent 150*a*-150 *e* can accept, refuse or ignore an event. When ignoring an event, the respondent neither accepts or refuses the event. Independent of whether a respondent accepts, refuses or ignores an event, the respondent can request additional details regarding the event. For example, the respondent 150*a*-150*e* can view a portion of an ECG wave form of a patient associated with the event, regardless of whether the respondent 150*a*-150*e* later accepts, refuses or ignores the event.

In response to receiving the communication 332*a*, the respondent 150*a* communicates a response communication 334*a* via the device 130*a* that includes an indication of an acceptance of responsibility for responding to the first communication 112*aa*. In response to receiving communication 332*b*, the respondent 150*b* communicates a response communication 336*b* that includes an indication of a refusal to accept responsibility for responding to the first communication 112aa. Accordingly, the status of the respondent 150*b* is set to being unavailable even though the status of the respondent's device 130*b* is available.

As a result, responsibility for responding to the first communication 112*aa* is assigned to respondent 150*a*. The respondent 150*a* is also referred to as the accepting respondent 150*a*.

In response to receiving the communication 334*a*, the notification server 160 transmits a third communication 338*a*-338*b* to the respondent devices 130*a*-130*b* previously receiving the second communication 332*a*, 332*b*. The notification server 160 transmits a third communication 338*a* to respondent device 130*a* and a third communication 338*b* to respondent device 130*b*.

The third communication 338*a*-338*b* indicates that responsibility for the first communication 112*aa* has been assigned. Preferably, in some embodiments, the third communication indicates an identity of the accepting respondent 150*a* that accepted responsibility for responding to the first communication 112*aa*.

Figure 3B:
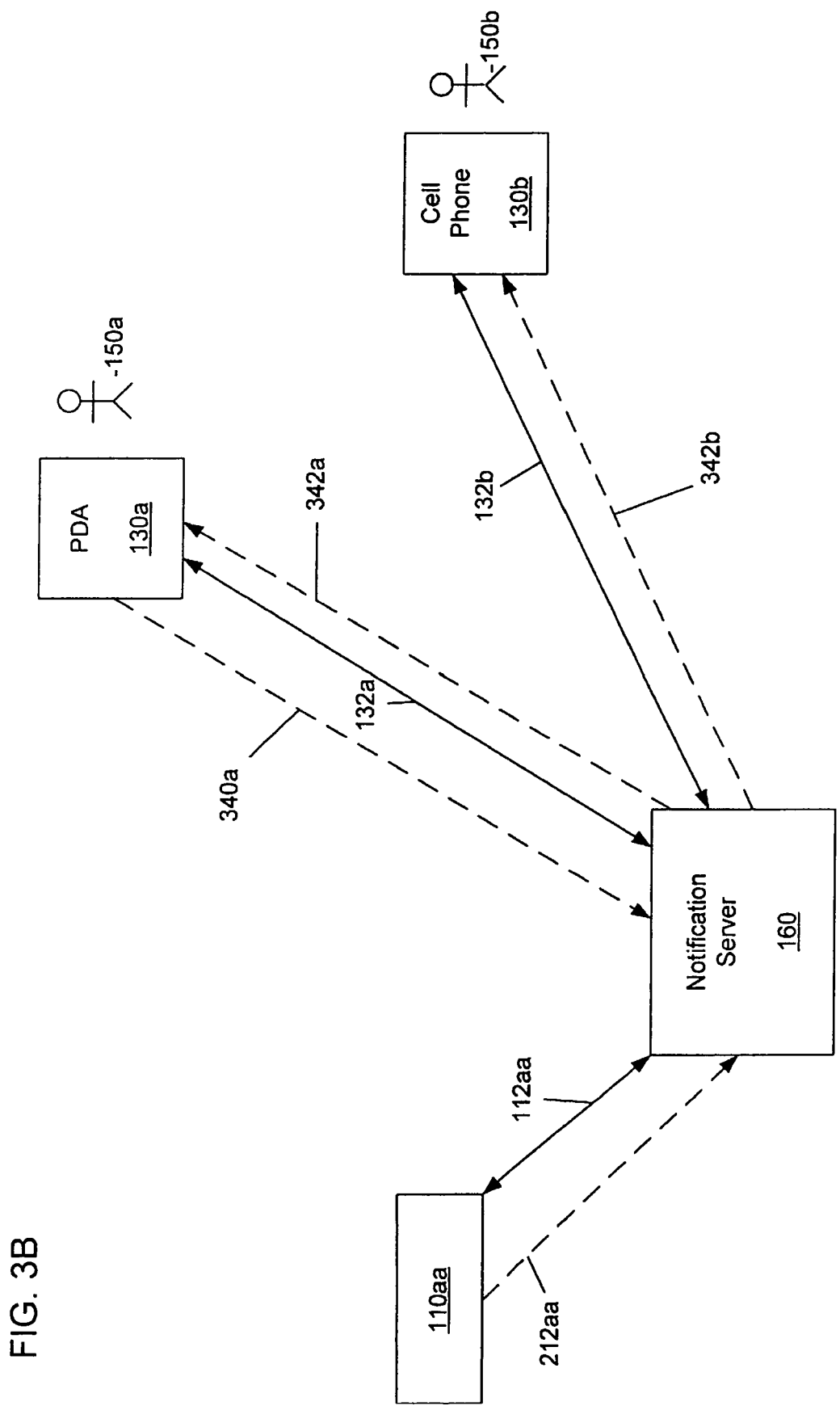
FIG. 3B illustrates an exchange of messages resulting in a revocation of acceptance of responsibility to respond to the first communication of FIG. 3A.

FIG. 3B illustrates an exchange of messages resulting in a revocation of acceptance of responsibility to respond to the first communication. In some circumstances, an accepting respondent 150*a* may later transmit a second response communication 340*a* indicating a revocation of a previous acceptance of responsibility to respond to the first communication 212*aa*.

In response to receiving the revocation communication 340*a*, the notification server 160 transmits a fourth communication 342*a*-342*b* to each of the respondent devices 130*a*-130*b* that received the third communication 338*a*-338*b* that was previously transmitted from the notification server 160. The fourth communication 342*a*-342*b*, also referred to as a revocation notification communication, includes an indication that the responsibility for the first communication 212*aa* that had previously been assigned to the accepting respondent 150*a*, has since been revoked.

In response to the revocation communication 340*a*, the notification server 160 re-performs the respondent notification procedure to search for and assign a respondent to accept responsibility to respond to the first communication 112*aa*. This procedure is now performed in the context of the additional information that the revoking respondent 150*a* of the first escalation level group is not available to accept responsibility for the first communication 212*aa*.

FIG. 3C illustrates an exchange of messages constituting escalating actions in pursuit of assigning acceptance of responsibility to respond to the first communication 102*aa*. Given that no respondent 150*a*-150*c* within the first escalation level group is currently available to accept responsibility, the notification server 160 performs escalating actions. Escalation may result from respondents revoking, rejecting, or ignoring events.

In this circumstance, the respondent 150*c* is associated with a first and a second escalation level group. The respondent device 130*c* is a member of both the first and the second escalation level group. Next, a current availability status for each of the respondent devices 130*c*-130*e* associated with the second escalation level group of respondent devices, is tested.

In this circumstance, unlike when tested in preparation for communicating to the first escalation level group, when testing at a later time in preparation for communicating to the second escalation level group, the respondent device 130*c* is available. In other words, the respondent device 130*c* is now currently available. The procedure to search for and secure a respondent to accept responsibility for responding to the first communication is re-performed as described above.

The respondent device 130*d* is a hallway message panel 130*d*. A hallway message panel 130*d* is a stationary device that is configured to receive and display a communication to people that are located proximate to it 130*d*. A hallway message panel is a "one-way" communication device in that it is configured to receive, but not transmit, a communication. A respondent 150*d* walking by the message panel can observe a received communication and respond to that communication via use of another respondent device 130*a*-130*b* or 130*d*-130*e*.

Generally, a respondent 150*a*-150*e* can also suspend an event via the patient monitor 110*aa*-110*c*, which has the same effect as accepting the event via the respondent device 130*a*-130*e*. In some embodiments, a suspended or accepted alarm re-alarms a period of time after the generation of the original alarm, such as after 90 seconds, if the condition that generated the original alarm continues to exist at the end of the period of time.

Next, the notification server 160 transmits the second communication 332*c*-332*e* to the available respondent devices 130*c*-130*e* of the second escalation level group. In this circumstance, the respondent 150*c* transmits an acceptance communication 334*c* to the notification server 160 to accept responsibility for responding to the first communication 212*aa*.

In response to the acceptance communication 334*c*, the notification server 160 transmits a third communication 338*c*-338*e* to respondent devices 130*c*-130*e* respectively. The third communication 338*a*-338*b* indicates that responsibility for the first communication 112*aa* has been assigned. In some embodiments, the escalating actions are now complete.

In some embodiments, a re-alarm will occur after the 90 seconds if the condition that caused the original alarm, continues to persist. In some embodiments, the respondent 130*c* is required to send an additional confirmation communication upon initiating care to the patient 102*a* (not shown) to substitute for, or to supplement, the re-alarm functionality.

Referring to other possible scenarios, hypothetically, if no respondent device of any escalation group associated with the patient 102*a* is available, then a second communication 332*x* is transmitted from the notification server 160 to at least one system administrator or manager 150*x*, and additional procedures are performed by the administrator or manager 150*x* to search for and assign a respondent to accept responsibility for responding to the first communication 212*aa*. Optionally, the notification server 160 further performs a step of broadcast transmitting the second communication 332*a*-332*e* to all potential respondents 150*a*-150*e*, where all potential respondents 150*a*-150*e* are the members of all of the escalation groups associated with the patient.

In other embodiments, optionally, before the notification server 160 automatically transmits a second communication 332*a*-332*e*, the operator can elect to re-direct or further direct transmission of the second communication from one associated respondent device 130*a*-130*e* to another respondent device 130*a*-130*x*, or to further direct transmission of the second communication 332*a*-332*e* to another respondent device 130*a*-130*x*, whether or not the other respondent device 130*a*-130*x* is associated with the patient 102*a* or an escalation group.

The respondent device 130*x* is not necessarily a system administrator nor a member of an escalation group. For example, one or more particular health care personnel may be available outside of their normal schedule at the time of time of attempting to respond to an event of interest. An operator can elect to re-direct or further direct transmission of the second communication to the one or more particular health care personnel in order to better respond to an event of interest. This feature allows an operator to take advantage of particular circumstances that may exist at the time of attempting to respond to the event of interest.

In other scenarios, the first communication 212*aa* could have been received from one of the other reporting devices 110*ab*-110*c*, instead off being received from the reporting device 110*aa*, as shown. Also, other respondents, such as respondents 130*c*-130*e* for example, could have been registered as members of the first escalation level group.

In accordance with the invention, the conditional transmission of the second communications 132*a*-132*b* is in accordance with the pre-determined set of rules, also referred to as the directives. The directives operate upon registration data associating respondent devices, respondents, escalation groups etc. The registration data can be revised during the operation of the system to that respondent/patient associations can be revised.

In some embodiments, a software module, referred to as a respondent identifier module, preferably executing on the notification server 160, inputs one or more characteristics of the first communication 212*aa*-212*c* and outputs one or more identities of the respondent devices 130*a*-130*e* and of the respondents 150*a*-150*e* in accordance with the directives. The respondent identifier module operates according to the directives and the registration data. Preferably, the directives and the registration data are stored into the repository which is accessible to the respondent identifier module. The respondent identifier preferably resides on the notification server 160.

In some embodiments, the repository resides on the notification server 160. In some embodiments, directives that encode the set of rules are entered into the repository via a central user interface. Likewise, the registration data can be entered via a central user interface or from the interface of the respondent devices 130a-130c, 130e.

In some embodiments, the user interface is provided by the central server 30. In other embodiments, the user interface is provided by the notification server 160. In some embodiments, the rules are expressed as a set of associations. The associations include those between reporting devices, reporting device addresses, patients, patient identifiers, respondents, respondent identifiers, respondent devices and respondent device addresses.

In some embodiments, the monitoring server 160, notification server 126 or the combined monitoring /notification server 128 provides a user interface to health care personnel (operator) to intercept and evaluate the information content of the first communication 212aa and to decide whether any actions should be further taken in response to the first communication 212aa, before proceeding with a performance of any further steps of an automatic respondent notification procedure. In some embodiments, the notification server 160 requires a confirmation from the operator as a pre-condition before transmitting a second communication 132a to any respondent.

For example, the operator, such as a medical technician, can arrange to evaluate (triage) the one or more events to at least confirm that the one or more events are real. As a result, the operator can elect to cancel, suspend, re-direct, further direct or to escalate notification of the one or more events.

Optionally, an operator can elect to suspend automatic processing of the first communication 212aa while evaluating whether actions should be further taken in response to it 212aa. Or, the operator can elect to cancel any further processing of the first communication 212aa if it is decided that no further actions are to be taken to respond to it 212aa. The notification server 160 is configured to record and to display the suspension or cancellation status of the first communication 212aa.

A respondent device 130a-130e can be any device that provides for bidirectional communication between the device 130a-130e and the notification server 160, or any device, such as the hallway message panel 130c, that provides for one way communication from the notification server 160 to the device 130a-130e with limited functionality at the device 130c. For example, the limited functionality at the device 130c could be for receiving notification only. The limited functionality would not include acknowledgement of receipt of the notification because the device 130c is not configured to transmit a communication.

A respondent device 130a-130e could have full graphics or text only capability. The respondent device 130a-130e could be owned by the health care facility, and used by each of multiple respondents 150a-150e working on each of multiple shifts. Or, the respondent device 130a-130e could be assigned to a respondent 150a-150e and travel with the respondent to work and home, and to possibly other health care facilities. In some circumstances, the respondent device 130a-130e, such as a cell phone 130b, could receive first (notification) communications 212aa-212c from multiple health care facilities during a period of time, such as during a work shift.

A respondent device 130a-130e can be implemented on a computing platform such as a hand held computer. A software application program (notification client program) can be executing on the computer in the background or the foreground with other medical or non-medical software applications. The (notification client) program can be configured to preempt other programs upon receipt of a communication from the notification server 160 when running in the foreground or background. Optionally, the respondent device 130a-130e can have bar code scanning functionality to scan identification of the patient, equipment or the respondent 150a-150e.

In addition to receiving a notification communication, the respondent device preferably 130a-130e can process and display other types of information including respondent access control, patient, event and respondent lists, waveforms, graphical and tabular trends and patient related data. Patient data can include patient name and identification, assigned location, actual location of the status reporting devices as reported using location technology, image, video and/or audio data associated with a patient.

The first communications 212aa-212c can report the occurrence of different types of events including patient (physiological) alarms, equipment alerts, patient location alert, or a nurse call button activation event, for example. In some embodiments, first communications (assistance request) can originate from a respondent 150a-150e to assist with providing care to a patient 102aa-102c. For example, a respondent transmits a first communication to access a crash cart for handling a cardiac arrest patient, or to receive assistance for lifting a patient 102aa-102c. Assistance requests can be directed to specific respondents or broadcast to any available respondent.

In some embodiments, the first communications 212aa-212c indicate a priority associated with each of one or more events. The first communications 212aa-212c may be processed and the second communications transmitted to the respondents 150a-150e based on the priority of each of the one or more events. Consequently, different respondents may receive different events base on the priority of each event and/or the type of event. For example, only a respiratory specialist is notified of respiratory problems. Or event priority can be based upon the identity of the associated patient. Events of a non-clinical nature, such as an equipment fault, can also be communicated.

In some embodiments, actions to acknowledge, cancel or suspend an event can be initiated from a respondent device 130a-130e or from the notification server 160 or from a device proximate to the patient's bedside. For example, a nurse at the notification server 160 or at a patient's bedside can correct a root cause of a first communication and cancel the first communication and any associated alarms and/or events.

In some embodiments, events are filtered to identify events of sufficient priority for notification to a respondent. Employment of event filtering can prevent notifications that can be a nuisance to respondents. Filtering can be based upon multiple, configurable filtering rules (criteria) and upon event priority. The filtering rules (criteria) can be customized for different patients. For example, in some embodiments, only events that are classified as life threatening are communicated to the respondents 150a-150e.

In some embodiments, filtering rules have restricted access and can only be revised by personnel having authorized roles and privileges. In other embodiments, at least some rules can be configured by a respondent 150a- 150e from a respondent device 130a-130 e or from another location such as a notification server 160.

In some embodiments, the respondents 150a-150e can assign themselves to particular patients and events associated with a first communication. In other embodiments, assignment can be performed by an administrator or manager using a PDA or Web Browser interface. In other embodiments, assignment can be performed automatically, referred to as automatic assignment, based upon various types of information including patient and respondent location, or upon the location of the respondent within the structure of the health care organization.

Preferably, the system provides to an administrator a user interface to access assignments and associations between patients, respondents, devices and health care units and events and statistics over time, preferably in graphical or tabular form. In various embodiments, the user interface is available from the notification server 160, the central server 30 or the respondent devices 130a-130e.

In some embodiments, automatic assignment can be performed based upon either an assigned location of a patient and/or of a respondent, or performed based upon an actual location of patient and/or respondent, as reported using location monitoring and reporting technology, like that described within the commonly owned U.S. patent application Ser. No. 11/263,050 titled "Attachment/Location Monitoring of a Signal Generating Entity".

In some embodiments, the actual location of a patient and/or respondent can be determined at a time before an occurrence of an event or in real time in response to an occurrence of an event. One or more respondents can be selected according to their proximity to a patient associated with a first communication.

While the present invention has been explained with reference to the structure disclosed herein, it is not confined to the details set forth and this invention is intended to cover any modifications and changes as may come within the scope and spirit of the following claims.

What is claimed is:

1. A method for responding to a communication regarding the status of a health care patient, comprising the steps of:
   receiving a first communication that includes information regarding the status of an associated health care patient;
   determining an identity of the patient and whether an event of sufficient priority has occurred in association with said patient based upon one or more characteristics of said first communication;
   determining an identity of each member of a set of one or more first level respondents, said first level respondents having an association with said first communication;
   determining whether at least one of said first level respondents is available to receive a second communication including information regarding said first communication, and if no first level respondents are available to receive said second communication, performing a set of escalation actions, or else
   transmitting said second communication to a respondent device associated with said at least one of said first level respondents that are available to receive said second communication; and
   determining if at least a first one of said first level respondents transmits a first response communication that includes an indication of an acceptance of responsibility to respond to said first communication within a predetermined period of time, and if not true, performing said set of escalation actions, and else if true, performing a step of assignment of said respondent to said first communication.

2. The method of claim 1 where if said step of assignment is performed, then performing a step of transmitting a third communication to each of said first level respondents as a notification of said step of assignment.

3. The method of claim 1 where at least one of said initial respondents transmits a second response communication that includes an indication of a refusal to respond to said second communication.

4. The method of claim 1 where if said first one of said first level respondents transmits a third response communication including an indication of a revocation of said acceptance of responsibility to respond, then a fourth communication to notify of said revocation is transmitted to said set of first level respondents, and said steps of claim 1 that are performed in association with said second communication are performed in association with said fourth communication.

5. The method of claim 4 where if no other first level respondent is available to accept responsibility, then performing said escalation actions.

6. The method of claim 1 where said set of escalation actions includes performing a step of raising a mode of escalation from a lowest first escalation level to a higher second escalation level and transmitting said second communication to a set of second escalation level respondents.

7. The method of claim 6 including a plurality of escalation levels and where at least one of said escalation levels includes the step of broadcast transmitting said second communication to all potential respondents and where all potential respondents include respondents associated with all of said plurality of escalation levels.

8. The method of claim 1 where said first communication is received at a notification server before said step of transmitting said second communication and where said notification server is configured to receive and to conditionally transmit said second communication to respondents.

9. The method of claim 8 where said notification server is configured to output a representation of said first communication and its characteristics and to output a representation of an availability of potential respondents to receive and accept responsibility to respond to said first communication.

10. The method of claim 9 where said notification server is configured to enable personnel to suspend, cancel, re-direct, further direct or escalate transmission of said second communication to one or more potential respondents in response to receiving said first communication.

11. The method of claim 1 where said first communication is transmitted from a reporting device associated with said patient and where a suspension or a cancellation of said first communication can be performed via said reporting device.

12. The method of claim 11 where said cancellation is communicated from said reporting device to said notification server and from said notification server to any of said respondent devices that have received said second communication.

13. The method of claim 8 where said notification server is configured to automatically suspend, cancel, re-direct, further direct or escalate transmission of said second communication to one or more of said respondents in response to receiving said first communication in accordance with predetermined directives.

14. The method of claim 8 where said notification server is configured to also output a representation of said second communication and a representation of any response communications transmitted from any of said respondent devices in response to said second communication, said response communications including refusal to respond and revocation of acceptance to respond to said first communication.

15. The method of claim 8 where said notification server is configured to also output a representation of a suspension or a cancellation of said first communication.

16. The method of claim 1 where said characteristics indicate that said first communication requires confirmation as a pre-condition before transmitting said second communication.

17. The method of claim 1 where said first communication includes information describing a measurement of the current status of a patient.

18. The method of claim 16 where said measurement indicates an alarm event condition requiring prompt attention from a respondent.

19. The method of claim 16 where said measurement indicates no condition that requires prompt attention from a respondent.

20. The method of claim 17 where said alarm event is based upon at least one physiological measurement of said patient.

21. The method of claim 17 where said alarm event indicates a current location of said patient.

22. The method of claim 1 where said first communication is transmitted from a reporting device associated with said patient and where a suspension or a cancellation of said first communication can be performed from the notification server.

23. The method of claim 6 including a plurality of escalation levels where said second communication is retransmitted to all potential respondents in the event that none of the potential respondents accepts responsibility.

24. The method of claim 1 in which the first communication indicates that the health care patient has moved beyond the permitted boundaries.

25. The method of claim 1 where said association between said first communication and said first level respondents is determined before an occurrence of said event based upon a location that is assigned to a patient and upon a location that is assigned to each of said first level respondents.

26. The method of claim 1 where said association between said first communication and said first level respondents is determined in response to an occurrence of said event based upon an actual location of a patient associated with said first communication and based upon an actual location of each of one or more potential respondents as indicated by a location monitoring and reporting technology.

27. The method of claim 1 where said association between said first communication and said first level respondents is determined before a time of an occurrence of said event based upon an actual location of a patient associated with said first communication and based upon an actual location of each of one or more potential respondents as indicated by a location monitoring and reporting technology.

28. A system for responding to a communication regarding the status of a health care patient, comprising:
- at least one reporting device that is configured for transmitting a first communication of status information associated with a health care patient;
- at least one respondent device that is configured for receiving a second communication that is transmitted in response to said first communication;
- at least one server that is configured to:
- receive said first communication;
- determine an identity of said patient associated with said first communication;
- determine an identity of each member of a set of one or more first level respondents, said first level respondents having a predetermined association with said first communication;
- determine whether at least one of said first level respondents is available to receive a second communication;
- transmit said second communication to said at least one of said respondent device that is associated with at least one of said first level respondents that is available to receive said second communication; and
- determine if at least a first one of said first level respondents transmits a first response communication to said server that includes an indication of an acceptance of responsibility to respond to said first communication within a pre-determined period of time, and if not true, performing said set of escalation actions, and else if true, performing a step of assignment of said respondent to said first communication.

* * * * *